US006589286B1

(12) United States Patent
Litner

(10) Patent No.: US 6,589,286 B1
(45) Date of Patent: Jul. 8, 2003

(54) EUSTACHIAN TUBE STENT

(76) Inventor: Jason Litner, 321 E. 13th St., No. 7B, New York, NY (US) 10003

( * ) Notice: Subject to any disclaimer, the term of this patent is extended or adjusted under 35 U.S.C. 154(b) by 0 days.

(21) Appl. No.: 09/952,569

(22) Filed: Sep. 12, 2001

(51) Int. Cl.[7] .................................................. A61F 2/36
(52) U.S. Cl. ......................................... 623/23.7; 604/8
(58) Field of Search ............................. 623/23.7, 23.64, 623/11.11, 10; 604/264, 268, 239, 8; 606/109; 138/158, 161, 119, 128, 109

(56) References Cited

U.S. PATENT DOCUMENTS

| | | | | |
|---|---|---|---|---|
| 3,093,223 | A | * 6/1963 | Federico | 138/158 |
| 3,807,409 | A | 4/1974 | Paparella et al. | 128/350 |
| 3,982,545 | A | 9/1976 | Silverstein | 128/350 |
| 4,015,607 | A | * 4/1977 | Wright, III | 623/23.64 |
| 4,568,337 | A | 2/1986 | Treharne, III et al. | 604/247 |
| 4,695,275 | A | 9/1987 | Bruce et al. | 604/264 |
| 5,047,053 | A | 9/1991 | Jahn | 623/10 |
| 6,027,532 | A | 2/2000 | Hobeika | 623/10 |

OTHER PUBLICATIONS

Wright, J.W., Jr., et al: Preliminary Results With Use of An Eustachian Tube Prosthesis. *The Laryngoscope*, 87:207–214, 1977.
Wright, J.W. III, et al: The Eustachian Tube Prosthesis Revisited. *ORL* 86:834–837, 1978.
Lesinski, S. George, et al: Does the Silastic Eustachian Tube Prosthesis Improve Eustachian Tube Function?, *The Laryngoscope*, 90:1413–1427, 1980.

* cited by examiner

*Primary Examiner*—David J. Isabella
*Assistant Examiner*—William H Matthews
(74) *Attorney, Agent, or Firm*—Mark A. Litman & Assoc. P.A.

(57) ABSTRACT

A Eustachian tube stent designed to maintain patency of the eustachian tube passage, comprising a flanged tubular body constructed of a biodegradable material capable of eluting a drug. The stent design is adapted specifically for the Eustachian tube environment. The stent is positioned in the Eustachian tube via the middle ear by insertion past the tympanic membrane. The flange secures the stent at the tympanic orifice of the Eustachian tube.

15 Claims, 2 Drawing Sheets

EUSTACHIAN TUBE STENT

BACKGROUND OF THE INVENTION

1. Field of the Invention

The present invention relates to an apparatus for long-term ventilation and drainage of the middle ear cavity via enhancement of the normal physiologic functions of the eustachian tube.

2. Background of the Art

Adequate ventilation and drainage is essential for normal middle ear function. The Eustachian tube is purported to function in middle ear ventilation, drainage, and protection Chronic Eustachian tube dysfunction has been implicated in the pathogenesis of many otologic problems and is thought to be a principal cause of surgical failures. Patients with chronic middle ear disease have often been shown to have a mechanical narrowing or stenosis of the Eustachian tube, usually at the isthmus (junction of the bony and cartilaginous portions). This stenosis prevents normal function of the Eustachian tube.

Various methods have been devised to restore middle ear ventilation and drainage in the setting of chronic Eustachian tube obstruction. These have included elaborate procedures to restore Eustachian tube patency such as Eustachian tube irradiation and complex surgical shunt procedures. These are highly morbid procedures that have failed to gain widespread acceptance.

Most surgical procedures performed at this time involve bypassing the blocked Eustachian tube by implantation of a surgical prosthesis, usually in the tympanic membrane (ear drum), for ventilation of the middle ear cavity via the external ear canal. An example of such a ventilation tube is that disclosed in U.S. Pat. No. 3,807,409 to Paparella et al. These devices are deficient for several reasons. The body naturally extrudes these prostheses over variable time intervals. While functioning, they create the dual problems of a tympanic membrane perforation and an embedded foreign body exposed to a non-sterile environment. In addition, placement of a ventilation tube at the time of tympanic membrane or middle ear reconstruction can disrupt graft healing. U.S. Pat. No. 4,695,275 to Bruce et al., describes another type of ventilation tube designed to resist extrusion from the tympanic membrane. This prosthesis can function for a longer period of time but has a high incidence of persistent ear drum perforation following extrusion or removal, in addition to the aforementioned deficiencies.

Several attempts have been made to create a prosthesis for permanent aeration of the middle ear cavity. These prostheses also ventilate the middle ear through the external ear canal, however, they require a more complicated surgical procedure for insertion. U.S. Pat. No. 3,982,545 to Silverstein, describes a silicone rubber tube inserted into the middle ear through a hole drilled in the bony external ear canal. This prosthesis requires frequent cleaning as it has a tendency to obstruct, especially when inserted simultaneously with chronic ear surgery. U.S. Pat. No. 5,047,053 to Jahn, describes a similar permanent ventilation tube composed of hydroxylapatite. This tube is capable of biointegration with the bony ear canal. However, it does not eliminate the problems of extrusion or obstruction. Once obstructed, a second surgical procedure is required to remove or replace it.

All of the aforementioned inventions seek to provide an alternative method for middle ear ventilation and drainage rather than attempting to resolve the obstruction of the Eustachian tube itself. Anatomical studies have demonstrated that middle ear secretions are propelled toward the Eustachian tube orifice and away from the tympanic membrane, thus limiting the utility of the above prostheses implanted in the tympanic membrane. These studies suggest that enhancement, rather than bypass of the natural drainage pathway, the Eustachian tube, would provide optimal ventilation and drainage.

U.S. Pat. No. 4,015,607 to Wright, III, discloses a prosthesis for implantation in the Eustachian tube designed to provide permanent middle ear ventilation. The design comprises a simple hollow silastic tube with an attached flange. Both preliminary results published by Wright, III et al. in Laryngoscope, pp. 207–214, vol. 87, 1977, and long-term results published in ORL, pp. 834–837, vol. 86, 1978, were promising in a highly selective group of patients. However, attempts to extend use of the prosthesis to cases of refractory otitis media were "almost universally disappointing" in that the lumen of the prosthesis was usually completely occluded. A simllar study by Lesinki et al. in Laryngoscope, pp. 1413–1427, vol. 90, 1980, failed to reproduce any positive results, revealing high rates of tube protrusion, extrusion, mucosal inflammation, and obstruction. Seventy-seven percent of these ears had to be re-explored with removal of the prosthesis.

U.S. Pat. No. 5,645,584 describes a tympanostomy tube used in the treatment of a middle ear disorder, which is made of pure titanium or a titanium alloy. The tympanostomy tube comprises an elongated tubular member having a lumen formed longitudinally therein, the tubular member having substantially uniform diameter over the length thereof. The tubular member defines a wall of substantially uniform thickness, and the wall has a concavity inwardly formed on a portion of the elongated tubular member in a circumferential direction at right angles to a longitudinal direction thereof. The concavity is spaced from one end of the tubular member to form a flange portion on the tubular member, the lumen being longitudinally different in diameter and having a smaller diameter at a position at which the concavity is formed than at a position at which the concavity is not formed.

Almost all permanent prostheses inserted in the body will eventually cause an inflammatory tissue response and either become obstructed by encrustation or rejected and extruded. Since all stent materials cause some degree of mucosal incorporation, removal of a permanent stent has the attendant risk of causing bleeding and tissue injury. A permanent prosthesis also carries risk of pressure-induced erosion and injury to the adjacent carotid artery. In addition, a permanent Eustachian tube prosthesis is not desirable in many circumstances, such as in pediatric patients, in whom Eustachian tube dysfunction tends to be transient.

SUMMARY OF THE INVENTION

It is an aspect of the present invention to provide a Eustachian tube stent of superior design that is specifically adapted to the Eustachian tube environment. Another aspect of this invention is to provide a stent that will remain in place for a sufficiently long period of time to effect condition mediation without promoting inflamatory tissue ingrowth and obstruction or causing discomfort to the patient. Yet another aspect of this invention is to provide a stent composed of a biodegradable material that will be absorbed in a predictable manner, thus obviating the need for a second surgical procedure to remove it. Still another aspect of this invention is to provide a stent that is capable of carrying and eluting a drug that will enhance Eustachian tube lubrication and opening of the tube, and will resist infection and blockage.

The present invention provides an apparatus for long-term ventilation of the middle ear cavity that solves all of the problems discussed above. The stent of the present invention is positioned in the Eustachian tube with its proximal end open to the middle ear cavity. The preferably eccentrically-placed flanges secure the proximal end of the stent at the tympanic orifice of the Eustachian tube and prevent migration of the stent. The stent is easily positioned in the Eustachian tube under direct visualization after the medical practitioner has incised or lifted the tympanic membrane. The stent is advanced under direct visualzation, preferably over a stylet, guide wire, or over a flexible endoscope. Once the stent is inserted, the tympanic membrane is allowed to heal without perforation or communication between the external ear and middle ear spaces. The stent may be inserted at any convenient opportunity, such as at the time of middle ear exploration or reconstructive surgery.

The stent is specially adapted to the Eustachian tube environment. It comprises a hollow tubular body, preferably consisting of a network of biodegradable polymeric fibers having a primarily longitudinal orientation. It maintains patency and enhances aeration and drainage without having to exert a radial expansile force on the Eustachian tube. The stent components preferably degrade at a programmed rate, the rate being designed to permit a pre-determined safe duration of mucosal contact. The stent is wide proximally but narrows past the stenosed isthmus of the Eustachian tube. The preferably, eccentrically-placed flanges project laterally so as not to interfere with normal middle ear mucociliary clearance at the superior and inferior aspects of the Eustachian tube. The flanges support the stent from slipping within the Eustachian tube. There is no specific ridge or structure on which they hook or are supported, as the tympanic orifice is a flat surface. However, the stellate (radial projection shape) shape supports the stent from slippage. The flanges also may be flexible and exert a radial force when compressed to lessen the radial projection. The stent falls short of the distal end of the Eustachian tube so as to prevent autophony and ascending infection. The distal end of the stent is collapsible or flexibly compressible so as to protect the middle ear from unsavory conditions in the nasal pharyrnx, including infection, excessive noise, or excessive positive pressures such as that produced by violent sneezing or coughing. While the entire stent may be somewhat flexible, it is one important embodiment that the distal end is more compressible than the proximal end. With that feature, with the Eustachian tube in the resting closed state, the distal end will be more collapsed/compressed than the proximal end. In this manner, the distal end will be significantly closed or collapsed while the proximal portion will maintain a constant opening pressure across the area of narrowing in the stent. The distal portion should be collapsed to prevent the sensitive middle ear and inner ear from being exposed to refluxed secretions and excessive noise or pressure.

DETAILED DESCRIPTION OF THE INVENTION

Figure 1:
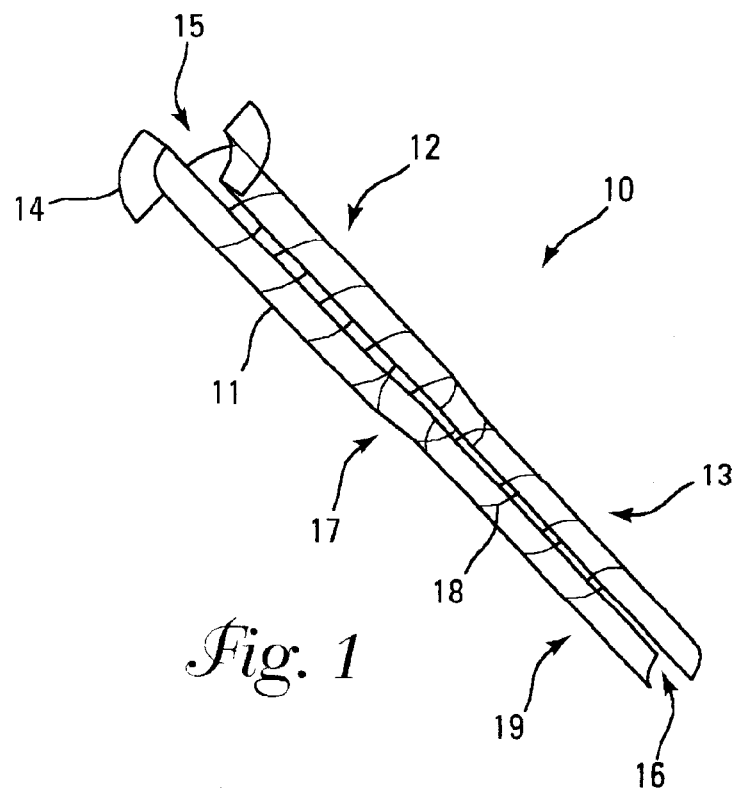
FIG. 1 is a perspective view of the present invention
Figure 2:
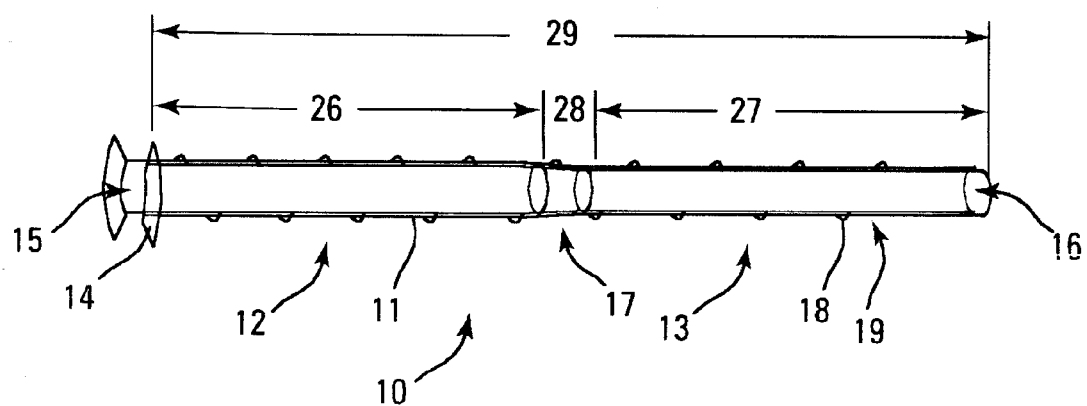
FIG. 2 is a side view of the prosthesis of FIG. 1
Figure 3:
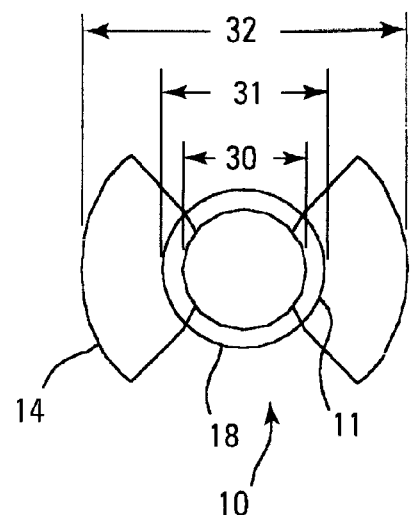
FIG. 3 is an end view of the proximal end of the prosthesis of FIG. 1

The detailed features of the preferred embodiment of this invention can best be seen by reference to FIGS. 1–3.

One embodiment of the Eustachian tube stent 10 of the present invention is shown in FIG. 1. Although the stent of the invention is desirably compressive by any construction (e.g., a single tube element with longitudinal openings that allow some compression), the following described embodiment is one of the preferred designs. This preferred design comprises a hollow tubular body consisting of two parallel rigid, semi-rigid, or stiff but flexible arms 11. The stent has a proximal end 15 and a distal end 16. The stiffness of the arms is acceptable within a broad range, even though certain ranges of flexibility are preferred. For example, the arms should be more flexible than a 1 mm×5 mm stainless steel flat sheet and less flexible than a 0.3 mm×5 mm 50,000 weight average MW polyvinyl chloride flat sheet. More preferably, the arms should be more flexible than a 0.5 mm×5 mm stainless steel flat sheet and less flexible than a 0.3 mm×5 mm 100,000 weight average MW polyvinyl chloride flat sheet. Each semi-rigid arm has an eccentrically positioned, laterally-oriented flange 14 projecting radially or outwardly from the proximal end 15 of the stent 10. The term 'eccentric' is used in the description of the invention has to do with the placement of the flange along the length of the stent, not with regard to its orientation with respect to its radial disposition from the stent. The parallel arms are preferably connected by supporting arches or a central supporting, discontinuous tube 18 at staggered intervals on the superior and inferior surfaces, or interior and exterior surfaces of the stent. The most distal segment 19 of the stent 10 lacks these supporting arches and is preferably somewhat compressible to allow normal passive Eustachian tube closure.

The description of the two-arm design is only a preferred embodiment for effecting compressibility in the core of the stent. A single core with a series of openings or an extended opening than enables compressibility of the structure (as opposed to compressibility of the material as would occur with a soft foam material) is also useful. There may be spacing elements within the structure that are compositionally compressible, while the stent composition itself is only structurally compressible. The term "two-arm" construction is used to describe a compressibility in the stent core. The core does not have to have two separately molded or extruded or otherwise manufactured elements, and may comprise a single element having two segments or two areas joined by at least one more flexible area which will preferentially flex. The flexibility/compressibility is desirable so that excessive forces exerted by the stent structure in a radial direction are prevented. The reduced pressure reduces the risk of perforation of the Eustachian tube and erosion into the adjacent carotid artery.

Figure 4:
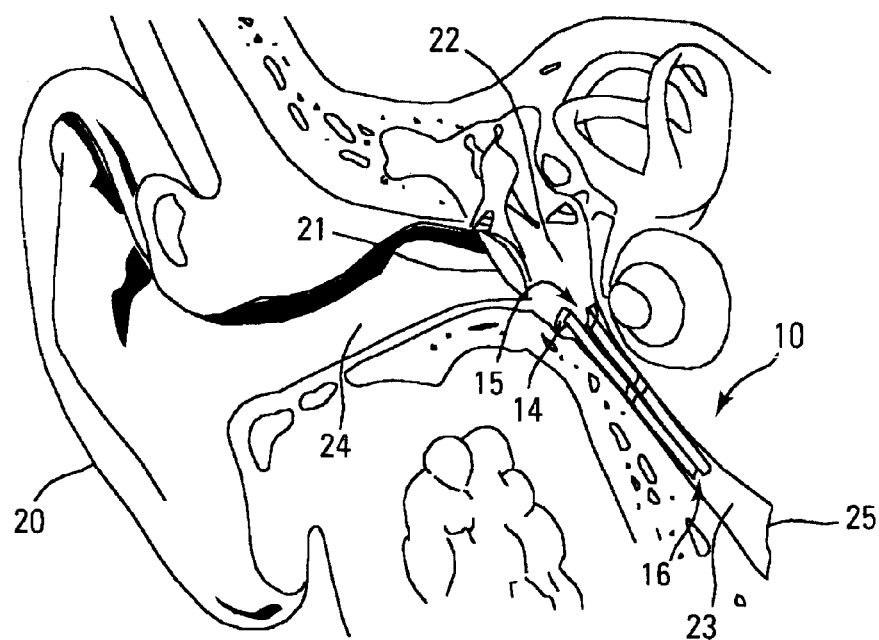
FIG. 4 is a view of the prosthesis of FIG. 1 positioned in the Eustachian tube

FIG. 4 shows a Eustachian tube stent 10 of the present invention properly positioned within the Eustachian tube passage. The figure shows a cross-section through the external ear 20 and ear canal 24. The stent is inserted past the tympanic membrane 21 and secured at the tympanic orifice of the Eustachian tube 23 by its flanges 14. The proximal end 15 of the stent 10 communicates with the middle ear cavity 22. The distal end 16 of the stent 10 is located about two thirds of the distance to the nasopharyngeal opening 25 of the Eustachian tube 23.

The dimensions of the stent can be varied in keeping with the variable dimensions of the human adult and pediatric Eustachian tubes. The stent 10 in FIG. 2 contains a proximal segment 12, which is located within the bony Eustachian tube 23 and has a length 26 of about 10 to 14 mm and an outer diameter 31 shown in FIG. 3 of about 2 mm. The distal segment 13 is located within the cartilaginous Eustachian tube 23 and has a length 27 of about 10 mm and an outer diameter 30 shown in FIG. 3 of about 1.5 mm. The proximal and distal segments are joined by an intervening segment 17 that traverses the Eustachian tube isthmus, having a length 28 of about 2 to 4 mm and an intermediate diameter between the diameters of the proximal end 15 and distal end 16 of the stent 10. The overall length 29 of the stent is about 22 to 28 mm. The outside diameter 32 of the flanged proximal end 15 is about 4 to 6 mm.

The tubular body and flanges of the present invention may comprise any structural material that is biocompatible and provides the necessary physical properties described herein. For example, the composition of the stent may comprise polymeric materials (both natural and synthetic), ceramic materials, composite materials, metals, metal oxides, and combinations of such materials. Biodegradable materials are preferred. One preferred structure comprises a network of biodegradable polymeric fibers having a caliber or average diameter of about 0.3 to 0.4 mm. The network may comprises a non-woven network, woven network, knitted network or the like. Poly-l-lactic acid is a particularly suitable material for stent construction, lasting up to 2 years or more in vitro before total degradation. However, alternative biodegradable polymers such as amylose and amylopectin derivatives, polyamides, polyvinyl alcohol, polyvinyl acetals, polyvinylpyrrolidone, polyacrylates, epoxy resins, and polyurethanes (mixtures thereof, blends with other ingredients, or copolymers thereof) are general, non-limiting examples of useful polymers. Although silicone resins could be designed to be controllably biodegradable, as is known in the art, they are not preferred. The stent may be coated by a polymer or coating composition, such as a carrier molecule such as hyaluronic acid, Perylenem™, heparin, and the like which may aid in lubrication, thrombo-prevention, bacterial resistance, and drug-carriage. The stent can be cross-linked or bound to a drug by gamma irradiation, chemical binding (as with binder or crosslinking molecules such as N-hydroxysuccinimide), or any other method. The stent may also be capable of the controlled release of a drug such as a surfactant, lubricant, antibiotic, antifungal agent, anti-inflammatant, or the like, which has been shown to decrease the opening pressure of the Eustachian tube.

The stent of the present invention is easily inserted, may be used concomitantly with middle ear surgery, and need not be removed by surgery. It is preferably degraded at a programmed rate, minimizing complications associated with indwelling effects. For example, the stent may be designed to degrade at a rate wherein structure may be completely removed by aqueous solution flushing in twenty-four months, eighteen months, twelve months or the like. The structure should preferably maintain sufficient structural integrity to maintain patency of the Eustachian tube for a designed period of time. For example, the period of treatment may be for a period between two weeks, two months, six months, twelve months or the like. A measure of the ability to maintain structural integrity would be that the stent can sustain a radially applied force without breaking (after the defined period of time) that is at least one-half of the structural force that can be sustained prior to implantation or immersion in a test environment. The stent presents a lubricious, biologically neutral surface capable of eluting a surface-active agent, thereby mimicking the function of the normal Eustachian tube. It is well-known in the art that chemical materials, including lubricants, medicaments, and the like, may be dissolved or dispersed in a polymer and this will bloom or exude or migrate from the polymer for local delivery of the material.

The foregoing description is considered to be illustrative, and modifications or improvements may be made by those skilled in the art without departing from the spirit and scope of the invention. It is intended, therefore, by the appended claims to cover all such modifications and changes as fall within the true spirit and scope of the invention.

Other References

J.W. Wright, III et al. "Preliminary results with use of an Eustachian tube prosthesis", Laryngoscope, vol. 87, 1977, pp. 207–214.

J.W. Wright III et al. "The Eustachian tube prosthesis revisited", ORL, vol. 86, 1978, pp. 834–837.

S.G. Lesinski et al. "Does the silastic Eustachian tube prothesis improve Eustachian tube function?", Laryngoscope, vol. 90, 1980, pp. 1413–1427.

What is claimed is:

1. A stent for placement in an Eustachian tube to maintain patency of the Eustachian tube comprising:

(a) a hollow tubular body having a proximal end and a distal end, the hollow tubular body comprising a compressible core that can extend along the Eustachian tube less than the full length of the Eustachian tube;

(b) the compressible core having two parallel arms connected by flexible connecting elements and (c) a radially-oriented flange extending laterally from the proximal end of the core.

2. The stent of claim 1 wherein said hollow tubular body lacks any completely circumferential supporting structures in order to minimize radial expansile forces on the Eustachian tube.

3. A stent for placement in an Eustachian tube to maintain patency of the Eustachian tube of a human comprising:

(a) a hollow tubular body having a proximal end and a distal end, the hollow tubular body comprising a pair of parallel arms that can extend along the Eustachian tube for less than the full length of the Eustachian tube (b) a radially-oriented flange extending laterally from the proximal end of each arm (c) connecting elements between the parallel arms at at least two positions along the length of the stent.

4. The stent of claim 3 wherein the parallel arms are separated at the distal end so that radially inward pressure of 0.1 kg/cm$^2$ against the arms in the distal region will cause the arms to flex inwardly and compress.

5. The stent of claim 3 wherein said hollow tubular body lacks any completely circumferential supporting structures in order to minimize radial expansile forces on the Eustachian tube.

6. A stent for placement in an Eustachian tube to maintain patency of the Eustachian tube comprising:

(a) a hollow tubular body having a proximal end and a distal end, the hollow tubular body comprising a compressible core that can extend along the Eustachian tube less than the full length of the Eustachian tube;

(b) a radially-oriented flange extending laterally from the proximal end of the compressible core within the Eustachian tube, wherein the stent further comprises:

(c) a proximal portion of said hollow tubular body structured for placement within a bony portion of the Eustachian tube, the stent having an outer diameter of at least about 1 mm up to 3 mm and a length between about 8 and 18 mm;

(d) a distal portion of said hollow tubular body structured for placement within a cartilaginous portion of the Eustachian tube, the hollow tubular body having an outer diameter of about 1 to 2.5 mm and a length of about 8 to 12 mm;

(e) the proximal and distal portions of said hollow tubular body connected by an intervening segment having an intermediate outer diameter between the diameters of the proximal and distal portions of said hollow tubular body, the total length of said hollow tubular body being between 22 and 28 mm;

(f) the proximal portion of said hollow tubular body having a greater outer diameter than the distal portion of said hollow tubular body in order to reduce erosive forces when within the Eustachian tube;

(g) the proximal end of said hollow tubular body having a pair of radially-oriented flanges separated by a gap at superior and inferior aspects of the proximal end of said hollow tubular body in order to allow for normal middle ear mucocillary clearance;

(h) the hollow tubular body comprising two parallel semi-rigid arms to allow flexibility to negotiate the Eustachian tube without causing perforation;

(i) the parallel semi-rigid arms of said hollow tubular body being oriented in a longitudinal direction in order to minimize radial expansile forces on the Eustachian tube;

(j) the parallel semi-rigid arms of said hollow tubular body connected by staggered arching supports over the superior and inferior aspects, lending strength while permitting mucocillary clearance over lateral aspects of said hollow tubular body; and (k) the distal portion of said hollow tubular body lacking the staggered arching supports over a most distal 3 to 5 mm length of the stent, allowing gentle collapse of the distal portion of said hollow tubular body during normal Eustachian tube closure in order to minimize ascending infection and noise-induced trauma, or the distal portion of said hollow tubular body having a semi-permeable membrane across its distal end in order to minimize ascending infection.

7. The stent of claim 6 wherein said hollow tubular body lacks any completely circumferential supporting structures in order to minimize radial expansile forces on the Eustachian tube.

8. The stent of claim 6 in which said hollow tubular body and flanges comprise a network of fibers, each fiber being about 0.2 to 0.6 mm in diameter.

9. The stent of claim 8 in which said hollow tubular body and flanges comprise a biodegradable polymer.

10. The stent of claim 9 in which at least one of said hollow tubular body and flanges contain or are coated with at least one compound selected from the group consisting of lubricants, anti-bacterial agents, anti-inflammatants, antifungal agents, drug carrying agent and anti-thrombogenic agents.

11. The stent of claim 10 in which at least one of said hollow tubular body and flanges are cross-linked to said at least one compound.

12. The stent of claim 11 wherein said at least one compound is a drug carrying agent capable of the controlled release of a drug.

13. The stent of claim 12 wherein said drug comprises a surface active agent.

14. The stent of claim 13 wherein the surface active agent comprises phosphatidylcholine.

15. A stent for placement in the Eustachian tube to maintain patency of the Eustachian tube comprising:

(c) a hollow tubular body having a proximal end and a distal end, the hollow tubular body comprising a compressible core having two parallel arms connected by flexible connecting elements, wherein the compressible core can extend along the Eustachian tube less than the full length of the Eustachian tube;

(d) the distal end of the stent being structurally compressible; and (e) a radially-oriented flange extending laterally from the proximal end of the core.

* * * * *